United States Patent
Funk et al.

(10) Patent No.: US 9,554,767 B2
(45) Date of Patent: Jan. 31, 2017

(54) METHOD AND APPARATUS FOR CONTROLLING X-RAY EXPOSURE

(71) Applicant: Triple Ring Technologies, Inc., Newark, CA (US)

(72) Inventors: Tobias Funk, Martinez, CA (US); Steve Denis Burion, San Francisco, CA (US); Kate LeeAnn Bechtel, Pleasant Hill, CA (US); Joseph Anthony Heanue, Oakland, CA (US); Brian Patrick Wilfley, Sunnyvale, CA (US); Augustus Percival Lowell, Durham, NH (US)

(73) Assignee: Triple Ring Technologies, Inc., Newark, CA (US)

( * ) Notice: Subject to any disclaimer, the term of this patent is extended or adjusted under 35 U.S.C. 154(b) by 0 days.

(21) Appl. No.: 15/018,792

(22) Filed: Feb. 8, 2016

(65) Prior Publication Data

US 2016/0166225 A1    Jun. 16, 2016

Related U.S. Application Data

(63) Continuation of application No. 14/496,346, filed on Sep. 25, 2014, now Pat. No. 9,254,114, which is a continuation of application No. 13/304,030, filed on Nov. 23, 2011, now Pat. No. 8,848,867.

(60) Provisional application No. 61/417,396, filed on Nov. 26, 2010.

(51) Int. Cl.
| | |
|---|---|
| *G01N 23/04* | (2006.01) |
| *A61B 6/00* | (2006.01) |
| *H01J 35/08* | (2006.01) |
| *H01J 35/14* | (2006.01) |
| *A61B 6/10* | (2006.01) |

(52) U.S. Cl.
CPC ............... *A61B 6/542* (2013.01); *A61B 6/405* (2013.01); *A61B 6/4028* (2013.01); *A61B 6/4035* (2013.01); *A61B 6/469* (2013.01); *A61B 6/5258* (2013.01); *H01J 35/08* (2013.01); *H01J 35/14* (2013.01); *A61B 6/107* (2013.01); *A61B 6/4241* (2013.01); *A61B 6/487* (2013.01); *A61B 6/504* (2013.01); *H01J 2235/087* (2013.01)

(58) Field of Classification Search
CPC ..... G01N 23/04; A61B 6/4028; A61B 6/4035; A61B 6/405; A61B 6/469; A61B 6/107; A61B 6/487; A61B 6/504; A61B 6/4241; H01J 35/08; H01J 35/14; G21K 1/10; G21K 1/025; G21K 1/04
USPC ............................................. 378/62, 145, 146
See application file for complete search history.

(56) References Cited

U.S. PATENT DOCUMENTS

2008/0285718 A1* 11/2008 Wedel ...................... A61B 6/06
378/150

* cited by examiner

*Primary Examiner* — Courtney Thomas
(74) *Attorney, Agent, or Firm* — Joseph T. Lin; Sabrina N. David

(57) ABSTRACT

The present invention pertains to an apparatus and method for adaptive exposure in imaging systems. An x-ray source for producing x-ray radiation and an x-ray detector for measuring amount of x-ray radiation passing through the human patient and striking the detector can be used. A tomographic image of the human patient or a tomosynthetic image of the human patient can be generated. Region of interest filtering and equalization filtering can be utilized. Filtering can be accomplished with a mechanical shield or shutter or with electronic control of the x-ray source.

15 Claims, 5 Drawing Sheets

| Table 1: Simulated contrast-to-noise ratio improvement for different iodine concentrations ||||| 
|---|---|---|---|---|
| Detector | 0.1 g/ml | 0.2 g/ml | 0.3 g/ml | 0.4 g/ml |
| integrating | 1 | 1 | 1 | 1 |
| Photon-counting | 1.10 | 1.10 | 1.09 | 1.09 |
| Energy resolving | 1.15 | 1.15 | 1.14 | 1.12 |

FIG. 4

METHOD AND APPARATUS FOR CONTROLLING X-RAY EXPOSURE

RELATED U.S. APPLICATION

This application is a continuation application claiming priority from the co-pending U.S. non-provisional patent application Ser. No. 14/496,346 entitled "METHOD AND APPARATUS FOR REDUCING X-RAY EXPOSURE," with filing date Sep. 25, 2014, which claims priority to U.S. non-provisional patent application Ser. No. 13/304,030, "METHOD AND APPARATUS FOR ADAPTIVE EXPOSURE IN X-RAY SYSTEMS," with filing date Nov. 23, 2011, which claims priority to U.S. provisional patent application, Ser. No. 61/417,396, entitled "Method and Apparatus for Adaptive Exposure in X-ray Systems," with filing date Nov. 26, 2010, all of which are hereby incorporated by reference in its entirety.

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Grant Nos. 1RC1HL100436-01 awarded by the National Institute of Health (NIH).

FIELD OF THE INVENTION

The present invention pertains to imaging systems. More particularly, the present invention pertains to region of interest filtering and equalization for x-ray imaging systems.

BACKGROUND

Many medical imaging procedures utilize x-ray radiation because x-rays are of energies, or wavelengths, that can penetrate most human tissue but are also absorbed or scattered to differing degrees by relatively dense tissues or organs and by bone. This property is useful as the relative intensity of x-rays emerging from a given irradiated region of a patient will correspond to the "x-ray density," i.e. the propensity to attenuate x-rays, of the internal structures within that region. Collected by an x-ray detector or simply incident on a fluorescent screen or x-ray film, emerging x-rays can be used to image the internal structures of the region. Furthermore, implements such as catheters may be inserted into a patient for surgical purposes and be tracked using x-ray imaging, or x-ray dense fluids may be injected into patients' veins so that blood vessel networks can be highlighted in subsequent x-ray images.

Some x-ray imaging procedures irradiate the patient for only a short period of time, as less than a second may be required to collect enough intensity data for a single x-ray image. However, some x-ray imaging are completed on a continuous basis such that a real-time video is generated for fluoroscopy and other image-guided procedures. Many surgeries, including the placement of stents and other cardiac procedures, have become much safer and requiring of significantly less recovery time since real-time x-ray imaging systems have enabled less invasive procedures.

While x-ray imaging is widely used for the aforementioned reasons, health risks associated with excessive exposure to high energy radiation, including x-rays, are recognized. The interaction of radiation with human cells and tissues may induce breakages or mutations which can develop into cancers over time. The probability of this type of cellular damage may be relatively insignificant from the exposure necessary to take a single image as may be necessary to analyze a broken bone, but may become less insignificant for patients who undergo relatively lengthy image-guided procedures, require multiple CAT scans, or undergo other multi-frame x-ray imaging procedures. Furthermore, cumulative amounts of scattered x-ray radiation may pose health risks for medical personnel attending x-ray imaging procedures on a regular basis.

Precautions taken in medical settings against significantly increasing individuals' cancer risk through x-ray exposure have included attaching collimation devices to x-ray sources which attenuate x-rays travelling in directions away from the region to be imaged and providing physical shielding for attendant personnel. Use of non-conventional x-ray imaging configurations such as inverse geometry systems have been explored to lower the overall amount of x-ray exposure necessary to obtain good-quality x-ray images by reducing scatter noise or other factors that degrade image quality.

However, existing precautions do little to tailor the amount of x-ray radiation being used during an imaging procedure to the specific patient, or regions within the patient, to reduce the amount of radiation exposure. What is needed is an imaging system capable of producing rapid high quality images while reducing the amount of radiation exposure.

SUMMARY

In one embodiment, an x-ray imaging system for imaging a human patient is provided with an x-ray source for producing x-ray radiation, an x-ray detector for measuring amount of x-ray radiation passing through the human patient and striking the detector, a controller for selecting a region of interest in the human patient and a filtering device coupled to the controller and x-ray source configured to reduce x-ray radiation to areas outside the region of interest in the patient. The filtering device can be an x-ray source controller for reducing amount of x-ray radiation generated by the x-ray source. The x-ray imaging system can include an x-ray source controller coupled to the x-ray source configured to limit x-ray radiation to a second region of interest in the human patient below a specified amount or less or an x-ray source controller coupled to the x-ray source configured to terminate delivery of x-ray radiation to an area in a second region of interest in the patient when x-ray radiation to the area reaches a predetermined threshold amount.

In another embodiment, an x-ray imaging system for imaging a human patient is provided with an x-ray source for producing x-ray radiation, an x-ray detector for measuring amount of x-ray radiation passing through the human patient and striking the detector, and a filtering device coupled to the x-ray source configured to limit x-ray radiation to the detector to a specified amount and less. The filtering device can be a shield or can be configured to limit x-ray radiation to a region of interest in the human patient to a second specified amount and less.

In another embodiment, a method for producing an x-ray image of a human patient is provided: producing x-ray radiation from an x-ray source, selecting a region of interest in the human patient, reducing x-ray radiation to areas outside the region of interest in the patient, and measuring amount of x-ray radiation passing through the human patient and striking a detector. X-ray radiation can be limited to a second region of interest in the human patient to a minimum amount required to achieve a specified signal-to-noise ratio for the x-ray image or a specified resolution for the x-ray image. X-ray radiation to a second region of interest in the human patient can be limited to a specified amount and less. Delivery of x-ray radiation to an area in a second region of interest in the patient can be terminated when x-ray radiation to the area reaches a predetermined threshold amount. Exposure of x-ray radiation can be selected for each of a plurality of projections of the region of interest.

In another embodiment, x-ray radiation is produced from an x-ray source, amount of x-ray radiation passing through the human patient and striking a detector is measured and x-ray radiation to the detector is limited to a specified amount and less. A region of interest in the human patient can be selected and x-ray radiation to the region of interest in the human patient can be limited to a second specified amount and less.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

FIG. 4 is a table displaying contrast-to-noise improvement for different iodine concentrations for procedures in which iodine has been used as a contrast agent.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

By way of brief overview, embodiments of the present invention will present manners by which the exposures of x-rays to at least one person can be minimized by region of interest filtering, or by one or more of the methods described herein or electronic region of interest filtering; equalization filtering, or by one or more of the methods described herein or utilizing electronic equalization filtration, or digital equalization filtration; modification of the x-ray spectrum, or by one of the methods described herein; and improving contrast using an energy resolving detector, or by the method described herein.

Figure 1:
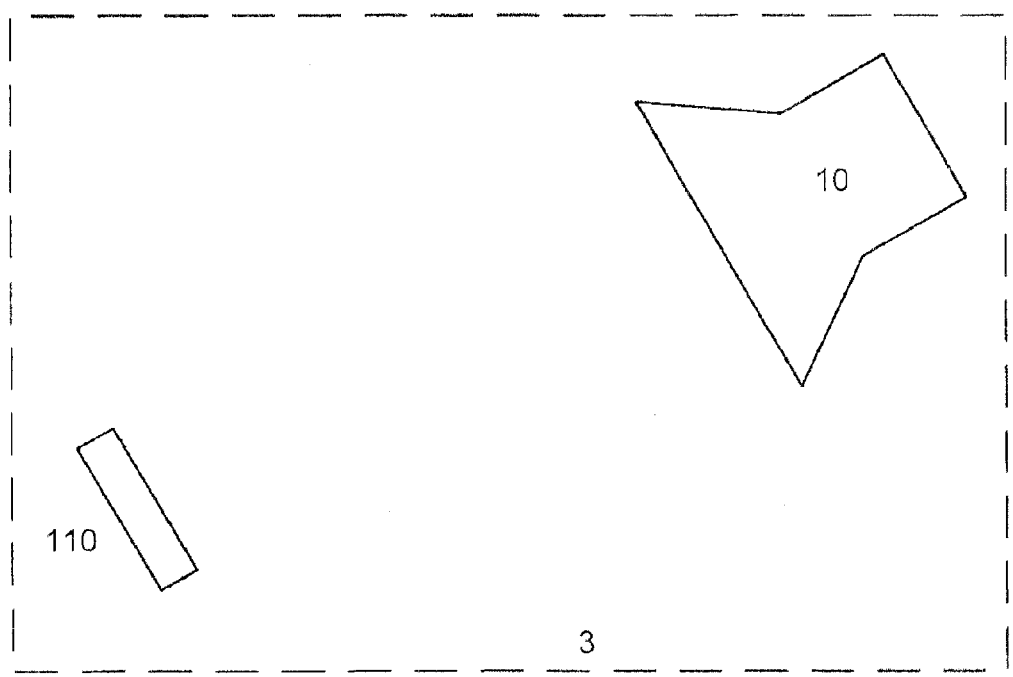
FIG. 1 is a diagram showing an exemplary x-ray imaging system of one embodiment of the present invention.

FIG. 1 is a diagram showing an exemplary x-ray imaging system of one embodiment of the present invention. An imaging system is disclosed in U.S. Pat. Nos. 5,651,047, 6,183,139, 6,198,802 and 6,234,671, entitled "Maneuverable and Locateable Catheters," "X-Ray Scanning Method and Apparatus," "Scanning Beam X-Ray Source and Assembly," "X-Ray System with Scanning Beam X-Ray Source Below Object Table," respectively, all of which are incorporated herein by reference in their entirety. Imaging system 3 can further comprise source 10 and detector 110. Source 10 can be a scanning-beam x-ray source or carbon nanotube x-ray source, discrete cathode x-ray sources, or other discrete x-ray sources. In one embodiment of the present invention source 10 can be a scanning beam x-ray source.

Figure 2:
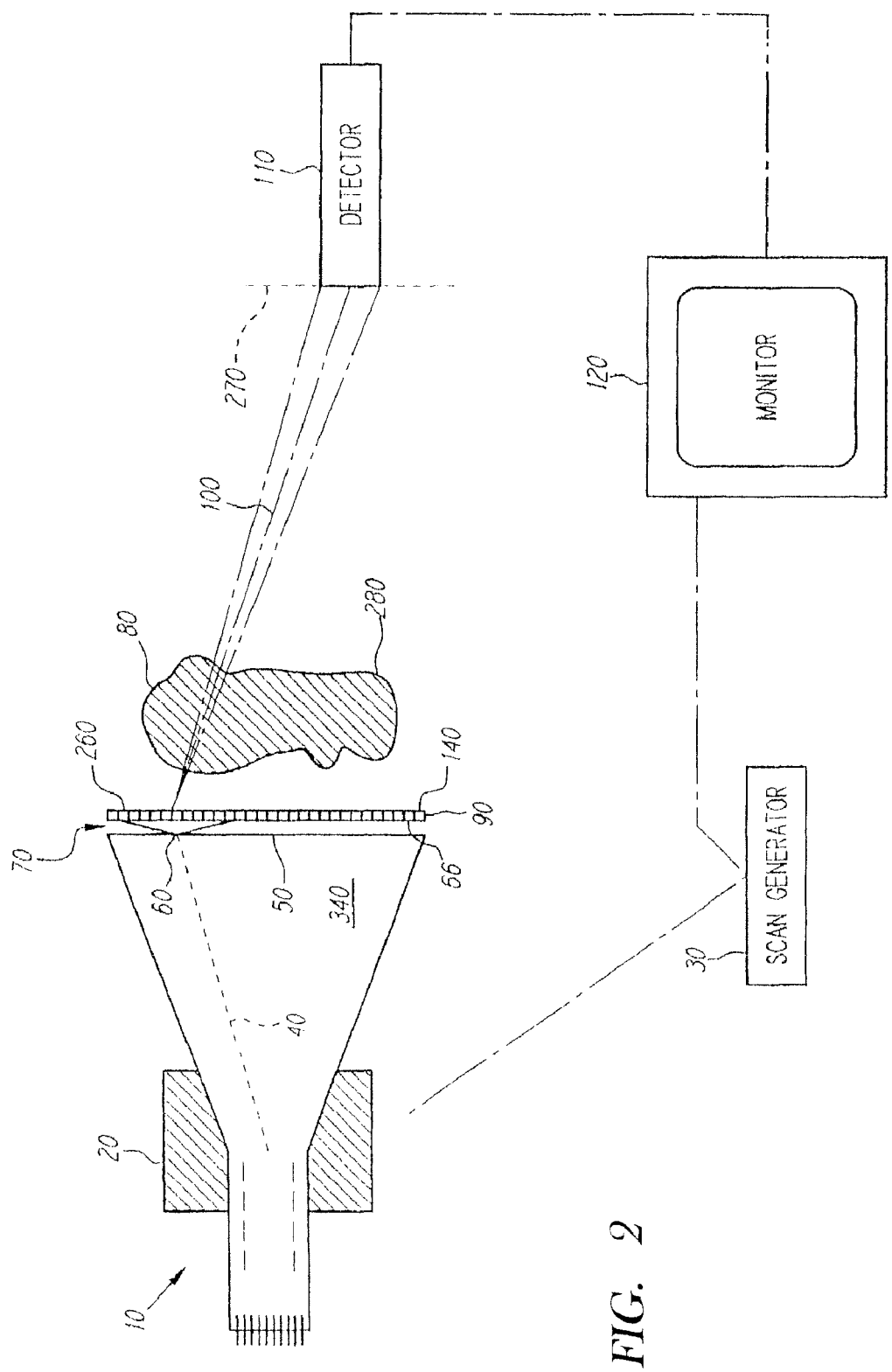
FIG. 2 is a diagram showing a portion of an exemplary scanning-beam x-ray imaging system of one embodiment of the present invention.

Use of scanning beam x-ray source 10 allows for utilization of a reverse geometry configuration for imaging system 3. In a reverse geometry configuration, a smaller detector can be used whereas a point source requires a much larger detector. The area of the detector can be 2, 3, 4, 5, 6, 7, 8, 9, 10, 11, 12, 13, 14, 15, 16, 17, 18, 19 or 20 percent of the area of the maximum field of view for given source configuration and detector distance from patient or any percentage in between such percentages or any range of percentages in between such percentages. In a reverse geometry configuration, the detector can also be located farther away from the patient than a detector with a point x-ray source. With a point x-ray source, the size of the detector required for a given maximum field of view size increases with the distance of the detector from the patient. The already large detector required with a point x-ray source becomes even larger with increasing distance. With a scanning x-ray source in a reverse geometry configuration, the size of the detector required for a given maximum field of view size decreases with the distance of the detector from the patient. Thus, the detector for scanning x-ray source 10 can be located with a distance from the patient of 1.3 m, 1.4 m, 1.5 m, 1.6 m 1.7 m, 1.8 m, 1.9 m, 2 m, 2.1 m 2.2 m, 2.3 m, 2.4 m, 2.5 m or any distance in between such distances or any range of distances in between such distances. FIG. 2 is a diagram showing an exemplary scanning-beam x-ray imaging system of one embodiment of the present invention. X-ray source 10 can be the x-ray source described more fully in U.S. Pat. Nos. 5,682,412 and 6,198,802, entitled "X-Ray Source" and "Scanning Beam X-Ray Source and Assembly" respectively, both of which are hereby incorporated herein by reference in their entirety.

X-ray source 10 can comprise deflection yoke 20 under the control of scan generator 30. Deflection yoke 20 can comprise one or more magnetic focus or deflection coils. The magnetic focus or deflection coils can be made with insulated electrical wire wound around a core. The core can be ferrite, steel, iron or other magnetic alloy. An electron beam 40 generated within x-ray source 10 can be scanned across target 50 within x-ray source 10 in a predetermined pattern. Target 50 can be a grounded anode target. The predetermined pattern can be a raster scan pattern, a serpentine (or "S" shaped) pattern, a spiral pattern, a random pattern, a gaussian distribution pattern centered on a predetermined point of the target, or such other pattern as may be useful to the task at hand. The serpentine (or "S" shaped) pattern can eliminate the need in a raster scan pattern for horizontal "fly back."

The images can be acquired, including reconstruction, and the exposure rates can be optimized using the methods described above and below, rapidly enough to create a continuous, real time video representation of the motion of the object, including organs such as one or more of the lungs, the heart, or other organs, or instruments, such as catheters or stents, or implantable objects such as valves, in real time.

The scanning-beam imaging system described herein can be used to generate a set of sequential planar images which can then be used to form a tomograph or a three dimensional display of the object 80. An image set can be analyzed to produce a three dimensional image consisting of a series of images at various depths by re-analyzing the data set with various values corresponding to planes of interest in the object 80.

Figure 3:
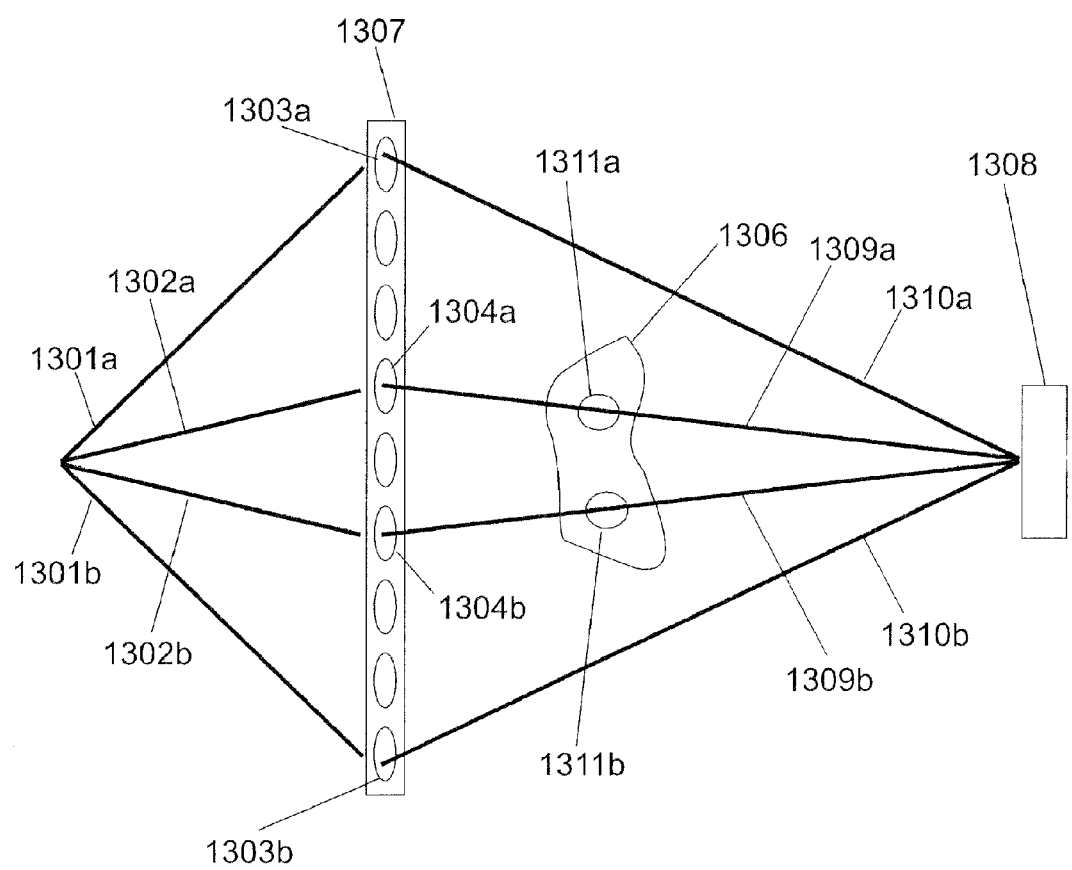
FIG. 3 is a diagram illustrating one embodiment of the present invention in which a region of interest has been defined within the patient volume.

FIG. 3 is a diagram illustrating one embodiment of the present invention. In FIG. 3 electron beams 1301*a* and 1301*b* impinge on focal points 1303*a* and 1303*b* of target 1307, and electron beams 1302*a* and 1302*b* impinge on focal points 1304*a* and 1304*b* of target 1307. Here, for simplicity, only one row of focal spots is shown, whereas in a preferred embodiment the target may be made of several rows of focal spots. When the electron beams 1302*a* and 1302*b* strikes target 1307 at focal spots 1304*a* and 1304*b*, x-ray beams 1309*a* and 1309*b* are created and measured by detector(s) 1308. An object, e.g. a human patient, to be imaged contains some region of interest 1306. Region of interest 1306 is shown here for simplicity as a single region, but in actuality could be 2, 3, 4, or more distinct regions of interest. In order to minimize the dose to the patient and reduce exposure to medical personnel, only the focal spots 1304*a* and 1304*b* and those between them are illuminated by the full electron beams 1302*a* and 1302*b*. As focal spots 1303*a* and 1303*b* would expose an area outside of region of interest 1306, patient dose is reduced by reducing electron beams 1301*a* and 1301*b* or redirecting the beams away from focal spots 1303*a* and 1303*b*. This process is referred to as region of interest filtering. It can be more specifically described as digital or electronic region of interest filtering, as the definition of at least one region of interest 1306 does not require the placement of mechanical components such as shutters, but instead is implemented by electronically controlling electron beams 1301*a*, 1301*b*, 1302*a* and 1302*b*.

In an embodiment of the present invention, detector 1308 is an energy resolving detector with two or more energy bins, preferably 10 or less bins, more preferably 5 or less bins, and most preferably 2 bins, and the contrast-to-noise ratio is optimized for a given contrast medium by weighting the number of detected x-rays in each bin by using the expression $$w(E) = \frac{1 - e^{-[\mu_c(E) - \mu_b(E)] \cdot d}}{1 + e^{-[\mu_c(E) - \mu_b(E)] \cdot d}}$$

as the weighting factor, wherein d is the thickness of the contrast medium, $\mu_c(E)$ is the energy dependent attenuation coefficient of the contrast medium, and $\mu_b(E)$ the attenuation coefficient of the background.

In another embodiment of the present invention, the exposure to x-rays of at least one person is optimized by modifying target 1307, and thereby modifying the shape of the x-ray energy spectrum, to best match the x-ray energy spectrum to one or more of: the needs of the procedure to be performed; the properties of the subject being imaged; the properties of the target organ to be imaged; any instrument that will be used during the procedure; and any contrast agents used during the procedure. The modification of target 1307 can involve the use of materials, wherein those materials are chosen from materials including but not limited to tungsten, copper, aluminum, beryllium, lead, rare earth elements including but not limited to gadolinium, and alloys or mixtures thereof.

It is an aspect of an embodiment of target 1307 that target 1307 comprises a tungsten layer in contact with the vacuum layer into which electron beam 1302*a* and 1302*b* impinges and creates x-rays 1309, and wherein the x-ray spectrum is modified by one or more layers of an additional material or materials. A modified target 1307 can comprise a beryllium sheet onto which a film of tungsten is deposited, while beryllium is in contact with a thin layer of cooling water, which is followed by thin aluminum sheet, and wherein the procedure may utilize iodine as a contrast agent, and wherein the procedure may be a cardiac intervention. FIG. 4 is a table displaying contrast-to-noise improvement for different iodine concentrations.

In a further embodiment, there is at least one additional layer comprising at least one rare earth metal between the tungsten film and the beryllium sheet, where the at least one rare earth metal can comprise gadolinium.

There are many ways that region of interest 1306 can be defined. In a preferred embodiment, a healthcare provider is presented with an image (a recently acquired frame) from which to define region of interest 1306 or multiple regions of interest. The image from which the health care provider defines region of interest 1306 and other regions of interest that will be exposed to x-rays can be the entire field of view of the system, or any subset thereof, including a previously defined region of interest. The health care provider can define the region(s) of interest in many ways, but in a preferred embodiment the region(s) of interest(s) are defined by the health care provider drawing the region on a display device, preferably using a dedicated stylus but in other embodiments using a finger or any other object.

In another embodiment of the present invention, the control and imaging portions of the apparatus are used to automatically define a region of interest that is optimal for the procedure to be performed, using methods chosen from a list including but not limited to: identifying an organ of interest, identifying a tumor, utilizing image data taken previously of the patient, using an algorithm that uses patient data including but not limited to height, weight, body mass index, age, sex, race, medical status or conditions, chest size, and/or length of arms or legs.

To further reduce the x-ray dose delivered to the patient as well as reduce the exposure to x-rays of health care providers, one embodiment of the present invention determines the minimum amount of x-ray radiation required to make a reconstructed image with a sufficient signal-to-noise ratio and resolution for the procedure to be performed, in at least one region of the object, preferably in more than one region, e.g. in region 1311*a* and region 1311*b*. Further, the apparatus then limits the x-ray dose to regions 1311*a* or 1311*b* to that minimum required amount. This is referred to herein as equalization filtering.

As shown in FIG. 3, there are two separate regions 1311*a* and 1311*b* to which equalization filtering may be applied. To apply equalization filtration, the x-ray absorbance of regions

1311*a* and 1311*b* are determined by exciting focal spots 1304*a* and 1304*b* with electron beams of known qualities. This causes the formation of x-ray beams 1309*a* and 1309*b* which pass through regions 1311*a* and 1311*b* and are subsequently detected by detector 1308. Based on this measurement, electron beams 1302*a* and 1302*b* are modified in a way that reduces the total x-ray dose to regions 1311*a* and 1311*b* to only that needed to achieve the signal-to-noise ratio required at the image resolution necessary to complete procedure being performed. The adjustable properties of electron beams 1302*a* and 1302*b* may be chosen from a list including but not limited to voltage, current, or duration. In a preferred embodiment the electron beams are raster-scanned over the focal spots on target 1307, dwelling on each targeted focal spot for a predetermined amount of time. The reconstructed image is formed from 2 or more raster scans of the electron beams over target 1307, and the equalization filtration is implemented by adjusting the number of times the electron beams dwell on each focal spot 1304*a* and 1304*b*. This method is herein referred to as digital equalization filtration.

In one embodiment of the present invention, the dose of x-rays to a patient is minimized by determining the amount of x-ray radiation detected by one or more pixels in one or more detectors, e.g. detector 1308, during an image acquisition and terminating the delivery of radiation to a region of the patient, e.g. region 1311*a* or 1311*b*, based on a threshold amount of measured x-ray radiation detected by the one or more detectors or detector pixels. In the digital equalization filtration method described above, this is implemented by measuring the amount of x-rays being detected by at least one detector or at least one pixel in at least one detector and during dwells of electron beam 1302*a* and 1302*b* on a focal spot 1304*a* and 1304*b*; determining a sum total of x-rays detected during one or more dwells of electron beam 1302*a* and 1302*b* on a focal spot 1304*a* and 1304*b*; and skipping future dwells to be performed on that focal spot 1304*a* and 1304*b* during that image acquisition when the sum total exceeds a predetermined threshold amount. This process is repeated for each focal spot 1304*a* and 1304*b* to be used. This embodiment has the advantage of a high signal-to-noise ratio for the determination of whether the signal measured has exceeded the threshold value.

In another embodiment of the present invention, the amount of x-rays detected during the first dwell of x-ray beam 1302*a* and 1304*b* on each focal point 1304*a* and 1304*b* is used to then compute the expected number of dwells required to measure a sufficient amount of x-rays to create an image of the required signal-to-noise and resolution, and that number of dwells is used during the imaging process. This determination is repeated for each focal spot to be used. This method has the advantage of being less computationally intensive but suffers from lower signal-to-noise than the previous embodiment.

Due to software or hardware limitations, it may be preferable to limit the number of changes in the number of dwells between subsequent focal spots during the raster scan of target 1307. This can be achieved by an algorithm that allows a range of values for the threshold value, for example by putting in some hysteresis that stops the number of dwells from bouncing up and down due to noise, for example Poisson or "shot" noise, in the number of x-rays arriving during the dwells during the raster scan.

It is preferable to perform equalization filtration in real time, i.e. during each image acquisition, by adjusting the exposure time or some other property of the electron beam to optimize the number of x-rays emitted from each focal spot as the imaging system runs. This has the advantage of not only minimizing the x-ray dose to the patient but also providing an optimized reconstructed image for each acquisition, for example each frame in a video image, by removing artifacts and issues due to, for example, heart rate and/or respiratory rate. However, the previously discussed embodiment of the present invention that minimizes the dose of x-rays to a patient by determining the amount of x-ray radiation detected by one or more detectors or pixels in one or more pixelated detectors during an initial image acquisition, and based on that measurement, delivering an optimal, reduced, amount of x-ray radiation to a region, e.g. region 1311*a* or 1311*b*, of the patient during one or more subsequent image acquisitions has the advantage of being less computationally intensive.

Other data and methods can be used to implement and refine equalization filtration, using methods chosen from a list including but not limited to: identifying an organ of interest, identifying a tumor, utilizing image data taken previously of the patient, using an algorithm that uses a predefined model of a region to be imaged and optionally includes patient data including but not limited to height, weight, body mass index, body fat percentage, age, sex, race, medical status or conditions, and/or size of a body region to be imaged, including but not limited to thickness, length, height, volume, and/or circumference, including but not limited to the size of the subjects chest, abdomen, waist, neck, head, arms, or legs, and using this information to modify the amount of radiation delivered to the various regions to be imaged. These techniques are preferably combined with the digital equalization filtration embodiments described above and/or combined with the electronic region of interest filtering described above.

In one embodiment of the present invention, image equalization is implemented using information about a reconstructed image, said image being a previously acquired image, e.g. an earlier frame. In this embodiment, it is preferable that the previous image be a recently acquired image, ideally in the range of 1 to 20 images previously acquired, and may be chosen from 1, 2, 3, 4, 5, 10, 15, or 20 images previous. It may be advantageous to utilize only image data from a subset, or region, within the final reconstructed image.

In another embodiment of the present invention, equalization filtration is implemented using a preliminary, interim reconstruction generated by x-rays detected from one or more detectors or one or more pixels in one or more detectors during a subset of the final dwell time on one or more focal spots. It is preferable that the subset of the final dwell time includes the first dwell and may optionally include data from the first and second; first, second, and third; first, second, third, or fourth; or any other combinations of the available dwells, including but not limited to during the first 3, 4, 5, 6, 7, 8, 9, 10, 11, 12, 13, 14, 15, 16, 17, 18, 19, or 20 dwells, or during the first ¼, ⅓, ¼, ⅔, or ¾ of the maximum number of dwells.

For digital equalization filtration, it is preferred that every time the electron beam dwells on focal spot 1304*a* or 1304*b*, the length of time it dwells on focal spot 1304*a* or 1304*b* is characterized by a predefined dwell time chosen from zero milliseconds (if region of interest filtering is simultaneously used and has determined that focal spot 1304 *a* or 1304*b* does not illuminate the region(s) of interest) to a predetermined non-zero dwell duration. The total dwell time for focal spot 1304 *a* or 1304*b* may then be the predetermined non-zero amount of time multiplied by the number of non-zero dwell time dwells for focal spot 1304 *a* or 1304*b*, and the dwell time for other focal spots may be similarly determined. The amount of delivered x-ray radiation can be adjusted by adjusting the number of non-zero duration dwells. The properties of the electron beam including but not limited to voltage, current, focusing, or dwell time per dwell can be the same for all focal spots used in target 1307, but these may also be adjusted to implement or refine equalization filtration.

For the digital equalization filtering described herein, it is preferred to reconstruct each image based on both the amount of x-ray radiation detected by the at least one pixel of the at least one detector 1308, and the number of non-zero dwell time dwells for each corresponding focal spot 1304a and 1304b. In an embodiment of the present invention, the amount of radiation detected by the at least one detector 1308 summed over the total number of dwells per image is divided by the number of dwells or the total dwell time of the electron beam 1302a or 1304b on the corresponding focal spot 1304a or 1304b and this normalized detected x-rays per dwell or per unit time is used in subsequent image reconstruction.

X-ray detector 1308 can include any usable technology, and may be chosen from a list including but not limited to: a photon counting detector, a charge-integrating detector, or an energy resolving detector.

In an embodiment of the present invention, detector 1308 is a photon counting detector, and the dwell time and/or the number of fixed dwells is modified by truncating the exposure of focal spot 1304a and 1304b to electron beam 1302a and 1304b when the number of photons detected by detector 1308 exceeds a pre-determined threshold number, and similarly truncated for other focal spots.

In an embodiment of the present invention, detector 1308 and/or other detectors are photon counting detectors or more preferably energy resolving detectors, and the dwell time and/or the number of fixed dwells is modified by truncating the exposure of focal spot 1304a and 1304b to electron beam 1302a and 1304b when the number of photons detected by detector(s) 1308 exceeds a pre-determined threshold number wherein the threshold number is modified based on one or both of: the number of photons detected in at least one energy bin by at least one pixel or detector 1308 during a previously dwelled upon different focal spot or focal spots; or the number of dwells before the threshold was reached during exposure of a previously dwelled upon different focal spot or focal spots during a given raster scan. This has the advantage that the threshold can be modified to minimize the number of changes in the number of dwells between subsequent focal spots in the scan of target 1307, simplifying the mechanism and the method, and/or allowing it to run faster.

Under an alternative embodiment of the present invention, x-ray dosage and radiation on object 80 or the patient and attending staff can be further reduced by use of adaptive methods and apparatus. Imaging system 3 may or may not be used in conjunction with a radiation source and may or may not be part of a radiation therapy system. X-ray imaging of the human body involves x-rays penetrating through different regions with highly varying attenuations; the intensity of x-rays reaching a detector depends on the amount the x-rays from a source were scattered and absorbed within the patient volume. Areas of the x-ray image can be overexposed with the result that object 80, the patient and attending staff can be exposed to unnecessary dose or x-ray radiation.

The adaptive methods and apparatus of one embodiment of the present invention can reduce x-ray dose and radiation and can be utilized for real-time x-ray imaging. Rather than acquiring the full-field image with a single exposure, imaging system 3 can use many exposures or projections of small areas of object 80 to generate the image, the number of exposures or projections can be as high as thousands. For a 7-inch field of view, up to 9,000 exposures or projections can be used. Multiple exposures or projections are possible through use of a scanning-beam x-ray source or a multi-pixel carbon nanotube x-ray source or discrete cathode x-ray source or other multi-pixel x-ray sources as source 10. Each exposure or projection can significantly overlap with neighboring exposures or projections, thus the exposures or projections can be redundant. Rather than using the same exposure for every projection, imaging system 3 exposes every projection with just sufficient exposure to obtain the desired image quality. For example, lungs may be a body part requiring less exposure to obtain an image of a given quality, as their attenuation characteristics permit the penetration of a relatively large percentage of incident x-ray radiation. Therefore, in an embodiment of the present invention utilizing a scanning-beam x-ray source or a multi-pixel carbon nanotube x-ray source or discrete cathode x-ray source or other multi-pixel x-ray sources, imaging system 3 may expose the lung to less radiation than other body parts that are relatively x-ray opaque, such as the heart, and still achieve sufficient image quality. Imaging system 3 can adjust exposures and radiation by using different tube voltages, beam currents, exposure times, repetitions of fixed-length exposures, or the combination of the former. One setting can be 120 kV tube voltage at 17 kW power and another setting can be 80 kV tube voltage at 9 kW power. Reducing the exposure or radiation is not the only benefit. Imaging system 3 also can define preselected regions of interest for increased image quality and other regions with lower image quality. Thus, regions of interest that require high image quality, can receive more exposure through increased repetition of fixed-length exposures of that region, different tube voltages, beam currents, exposure times, or the combination of the former.

Under an alternative embodiment of the present invention, source 10 can be a scanning-beam X-ray source. Electron beam 40 can be swept across X-ray target 50 and dwells at distinct focal spot 60 positions for a predetermined exposure time, which depends on the frame rate and the size of field of view. At a frame rate of 15 fps (7" mode field of view), the exposure time is 8 μsec. This exposure time is broken into 1 μsec illuminations (rescans) separated in time. For given material selection and dimensions of x-ray target 50, use of 1 μsec illuminations can keep the temperature of x-ray target 50 below desired maximums (maximums being set by the potential of the target to "burn out" when overheated by the incident beam in a localized region). Thus, every focal-spot position is rescanned several times. Different size or aspect ratio of field of view can also be used, 5"×5", 5"×10", etc, or, 6", 7", 8", 9", 10", 11", 12", 13", 14" or 15".

Imaging system 3 can utilize equalization or region of interest filtration or both. For both equalization or region of interest filtration, offline implementation or real-time implementation can be utilized. Imaging system 3 can acquire images from up to 9,000 different focal-spot positions for each full-field image. Each acquisition can be repeated up to 8 times (8 rescans). With 7" field of view, this results in a frame rate of 15 fps. Alternatively, each acquisition can be repeated 2, 3, 4, 5, 6, 7, 9, 10, 11, 12, 13, 14, 15, 16, 17, 18, 19 or 20 times (rescans). Imaging system 3 can aggregate the rescans or it can save each rescan separately (rescan images). Each rescan can be saved as a separate file and can be buffered. Alternatively, the rescans can be aggregated immediately.

Under an alternative embodiment of the present invention, imaging system 3 can implement equalization filtration using separate or aggregated rescan images. In this embodiment, imaging system 3 may first determine a target number of photons per detector image. It may then determine the number of photons in the rescan image(s) and aggregate rescan images until at least the target number of photons is reached or all 8 rescans are added. This procedure yields a "rescan map" detailing how many rescans are needed per focal spot position and a modified detector image file that can be reconstructed with the reconstruction engine.

Equalization filtration not only saves dose but can be a very effective way to compress dynamic range and thereby improve image quality. As previously discussed, equalization filtration can dynamically and automatically vary the exposure depending on the opacity of the region exposed. Hence, it can compress the dynamic range by reducing exposure significantly in translucent areas such as the lung field and maintain exposure in more opaque regions.

Under another embodiment equalization is performed by variation of the beam current and the beam current is adjusted according to the flux measured at the detector. Importantly the beam current can start at low values to not saturate the detector even with no attenuator, e.g. no patient, present. With an attenuator present this low beam current will result in a very low flux being detected at the detector. Feedback relaying detected flux can lead to up-regulation, i.e. increasing, of the beam current until desired flux is achieved. The up-regulation can be done during a single exposure or implemented via rescans.

Figure 5:
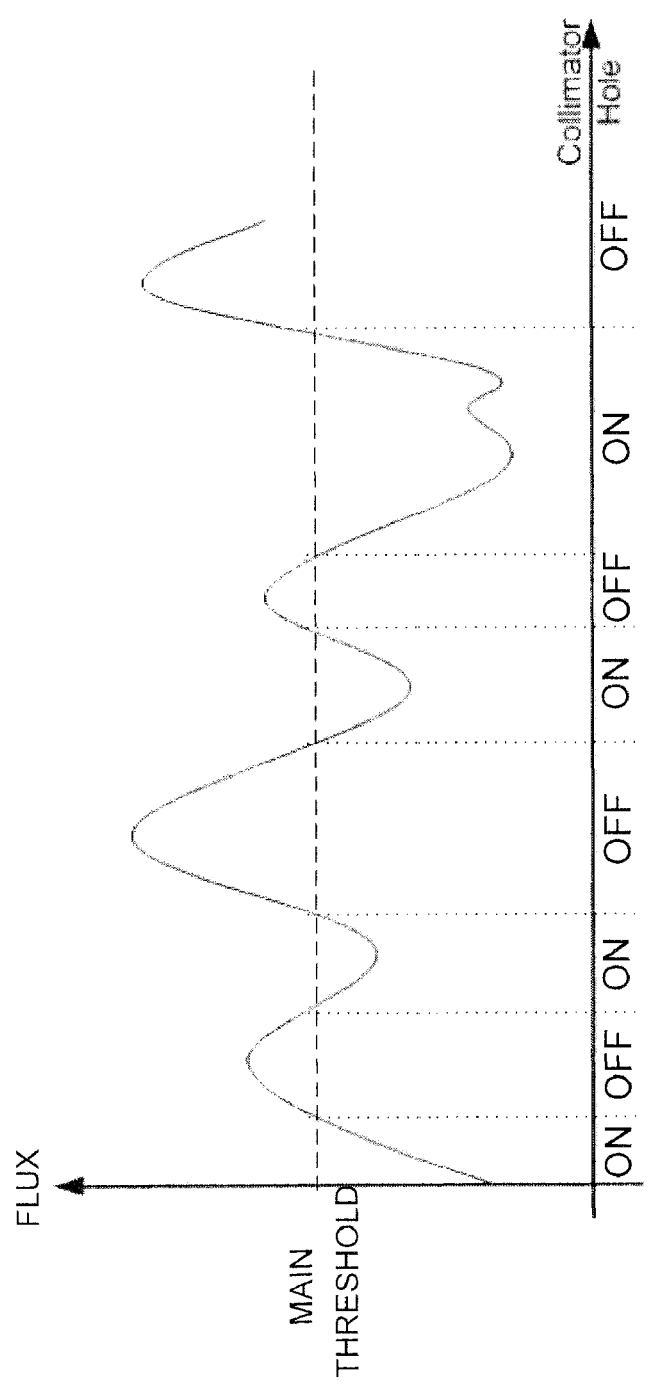
FIG. 5 is a plot illustrating a manner of equalization filtration of one embodiment of the present invention.

FIG. 5 is a plot illustrating a manner of equalization filtration of one embodiment of the present invention. In this embodiment, equalization filtration can be implemented by performing the first scan across the entire field of view or part of the field of view. A "main threshold" can be determined to limit exposure in each partial image of each rescan. Once desired exposure level or threshold has been achieved, the x-ray beam in partial images can be turned off or the x-ray beams associated with particular collimator holes can be turned off. With proper threshold value, partial images or collimator holes receiving exposure above the threshold will be turned off. In this manner, the dynamic range of exposure values can be compressed and dose can be saved. Image quality can be improved by reducing exposure in the light areas thus reducing the dynamic range.

In FIG. 5, the x-axis, labeled "Collimator Hole" represents the position of the scanning beam over subsequent apertures in collimation grid 90; it could also be viewed as a temporal axis, where the units of time are equal to the dwell time for a single aperture. The y-axis indicates the amount of x-ray flux emitted from an aperture that reaches detector 110 after penetrating some amount of patient volume. It can be seen that aperture 140 will be scanned by beam 40 or otherwise illuminated, i.e. "on," until the amount of x-ray flux from a given aperture reaching detector 110 exceeds the main threshold, at which point the electron beam is switched "off." If the flux drops below the main threshold, the electron beam is switched on again, and so forth.

Under an alternative embodiment of the present invention, equalization filtration can be done by calculating the rescan map in real time while the image is acquired. Implementation of the rescan map allows imaging system 3 to perform an equalization filtration scan in hardware, turning on or off the x-ray beam depending on how many rescans are needed. A complication is that there may be a hardware limit related to the grid control on the electron beam that limits the number of times that the x-ray beam can be turned on or off (number of switches) during each image acquisition frame. Such a limitation results from impedance, resistance, capacitance and inductance characteristics of the hardware. To limit the number of switches, equalization filtration can be modified by not only relying on a single threshold but rather considering a band of target counts, effectively low-pass filtering the rescan map. With a single threshold as in FIG. 5, imaging system 3 may switch 774 times or more. With a threshold band of target counts, imaging system 3 could reduce the number of switches to 548 or some other number below 774 or the number of switches experienced with a single threshold. With adjustment of threshold settings in the threshold band, imaging system 3 could further reduce the number of switches to 463 or some other number below 774 or the number of switches experienced with a single threshold.

Imaging system 3 can implement equalization filtration using a threshold band, comprised of an upper maximum threshold and a lower minimum threshold, of target counts by saving or tracking exposure (flux) for each area or collimator hole in the rescan map. As imaging system 3 performs a scan, when the exposure or flux for an area or collimator hole increases from a level below a maximum threshold to a level just above the maximum threshold, the x-ray beam for the area or collimator hole is turned off. When the exposure or flux for an area or collimator hole falls below the maximum threshold, the x-ray beam for the area or collimator hole remains off. When the exposure or flux for an area, or collimator hole decreases further to a level below a minimum threshold, the x-ray beam for the area or collimator hole is turned on. When the exposure or flux for an area or collimator hole increases above the minimum threshold, the x-ray beam for the area or collimator hole remains on. When the exposure or flux for an area or collimator hole increases above the maximum threshold, the x-ray beam for the area or collimator hole will be turned off. At different angles, imaging system 3 can save between 33% and 60% dose with an average dose saving of 47% using equalization filtration. Alternatively, dose saving of 41%, 43% or 45% of primary photons can be achieved.

If visualized using FIG. 5, the threshold band may appear as a horizontal line positioned higher on the y-axis than the main threshold representing the maximum threshold and a horizontal line positioned lower than the main threshold representing the minimum threshold. The state of the collimator hole would only switch from "on" to "off" when the flux transitioned from below to above the maximum threshold and would only switch from "off" to "on" when the flux transitioned from above to below the minimum threshold.

Under an alternative embodiment of the present invention, equalization filtration can be done by calculating the rescan map from a single frame of a real-time video and use it for the subsequent frame. Implementation of the rescan map in this manner allows imaging system 3 to perform an equalization filtration scan in hardware, thus turning on or off the x-ray beam depending on how many rescans are needed. This embodiment can be used with a single threshold or a threshold band.

Under an alternative embodiment of the present invention, imaging system 3 can utilize region of interest filtration, and two or more regions of interest can be selected. The first region of interest may maintain full image quality, with 8 rescans or the maximum number of rescans, and the second region of interest may only be imaged at significantly reduced image quality, with 1 or 2 rescans or a lower number of rescans than full image quality. Outside the second region of interest, the beam may turned off entirely via electronic collimation or another method. The rescan images can be aggregated based on the selection by the user or based on automatic or predetermined selection by imaging system 3. The resulting detector images can be reconstructed and can be evaluated for image quality and dose savings. The user can toggle between region of interest filtration and standard acquisition mode on a frame by frame basis. Collimation can be but does not have to be toggled as well.

Region or regions of interest can be selected by the user or selected by imaging system 3 based on automatic or predetermined selection. After selection, imaging system 3 can define and implement region or regions of interest by deploying a mechanical shield or shutter to block electron beam 40 before x-ray target 50 or the x-ray beam after x-ray target 50. Shield or shutter can be made from tungsten, tungsten copper, tungsten alloy, lead, lead antimony, lead alloy, tantalum, tantalum alloy or other material with a high atomic number. (Materials with a high atomic number may successfully shield x-rays more so than materials with low atomic numbers.)

Under an alternative embodiment of the present invention, region or regions of interest can be selected by the user or selected by imaging system 3 based on automatic or predetermined selection from a variety of shapes including without limitation, circle, oval, ellipse, square, rectangle, triangle, polygon and quadrilateral shapes. The region or regions of interest can also be the entire field of view except the regions within the shape selected or the regions excluded by the shape. The size of the region or regions of interest can be any size or range of sizes up to the size of the field of view. In one embodiment of the present invention, the region of interest is set to the size of a human heart or one chamber of the human heart and is intended to expose only the heart or selected chamber to radiation. In another embodiment of the present invention, the region of interest is the size of human ovaries and is intended to exclude radiation from the ovaries.

To implement region of interest filtering, imaging system 3 can perform an initial scan across the entire field of view. Alternatively, imaging system 3 can utilize a previous saved scan or image. Imaging system 3 can also perform one or more rescans across the entire field of view. Imaging system 3 can then perform one or more rescans based on the shape selected or shape excluded at the size of the region of the interest. The rescan would only involve exposure for some area or collimator holes corresponding to the shape selected at the size of the region of interest. The rescan may involve all of the collimator holes within the shape selected or a portion of those collimator holes but would not involve areas or collimator holes outside the shape selected. In the example of a shape excluded, the rescan would only involve exposure for the area or collimator holes outside the shape excluded at the size of the region of interest. Imaging system 3 can also perform one or more rescans based on one or more additional shapes selected or shapes excluded at one or more sizes of the region of the interest.

Under one embodiment of the present invention, imaging system 3 performs one initial scan and one rescan across the entire field of view, two rescans or one additional rescan across a rectangular region of interest corresponding to half of a human heart, and eight rescans or six additional rescans across a smaller region of interest within the rectangular region of interest. The entire field of view receives one initial scan and one rescan. The rectangular region of interest receives one initial scan and two rescans and the smaller region of interest within the rectangular region of interest receives one initial scan and eight rescans. Dose savings of up to 82% of the primary photons can be achieved utilizing this region of interest approach.

Under an alternative embodiment of the present invention, the specific region of interest can vary in position in the field of view over time. The region of interest can be a selected shape (e.g. circle, oval or ellipse) of a specified size that follows a contrast agent as it flows through vessels in the heart. The region of interest can be automatically selected by, for example, following the tip of a catheter or by following the bolus of a contrast medium. The region of interest can follow the edge of the contrast agent as it moves through vessels in the heart. The region of interest can also be time-based in a manner which tracks the motion of an organ such as the heart. The region of interest can be the area of the field of view experiencing motion.

Alternatively, the region of interest can be calculated by imaging system 3. In a tomographic or tomosynthetic application, the user can select a single plane or multiple planes of interest. The user can select the region or regions of interest in the selected plane or planes; the region of interest can be selected by the user in three dimensions. Imaging system 3 can then track the region of interest or regions of interest in following frames by incorporating motion within the field of view and calculating the relative position of the region of interest or regions of interest.

Under an alternative embodiment of the present invention, equalization filtration can be combined with regions of interest to achieve maximal dose savings without detracting from the high image quality desired.

If target 50 includes a tungsten film, x-ray may be emitted through two mechanisms: Bremsstrahlung radiation, a direct results of the sudden deceleration of electrons by collision with heavier target particles, and K-line radiation, a result of incident electrons knocking target electrons out of their atomic "K" shell and other target electrons shedding energy to fill these created vacancies. Bremsstrahlung radiation takes on a spectrum of wavelengths and is the primary mechanism by which x-rays are emitted whereas K-line radiation emits a specific wavelength characteristic to the atomic structure of tungsten or target material and is the less prevalent mechanism.

Under an alternative embodiment of the present invention, the beam hardening filter is brought into close proximity of the tungsten film in x-ray target 50 and emitted K-line radiation can have a similar spatial extent as the primary (Bremsstrahlung) radiation and can be useful for imaging. X-ray target 50 can also have an additional film with a rare earth that has K-lines particularly well suited for imaging. Specifically, the rare earth can provide large contrast in iodine, a contrast medium used in interventional cardiology. Various rare earths can be used (e.g. Er, Gd, Dy, Sm) with different thicknesses (10 μm to 150 μm) and X-ray tube potentials (60 kVp to 90 kVp). A 150 μm layer of erbium in x-ray target 50 at 80 kVp can result in a low dose. The dose can be 87% of that found with 1 mm iodine using 0.1 mm Copper beam hardening filter, 70 kVp X-ray tube potential and maximum electron beam current of 210 mA. A reduced Er layer thickness of 120 μM can also be used and Er can be used in x-ray target 50. For the beam hardening filter the dose can be 96% with 1 mm iodine using 0.1 mm Copper beam hardening filter, 70 kVp X-ray tube potential and maximum electron beam current of 210 mA and for the integrated case it can 89%. Thus, using Er in the target can save 7.5% of the dose compared to using it as a beam hardening filter.

From a dose standpoint, a 150 μM Erbium target can be utilized. Er can be a significant thermal resistor that slowed the time to equilibrium temperatures significantly. A more convenient measure of time to equilibrium is the time to maximum temperature in the Be layer. With 1 mm iodine using 0.1 mm Copper beam hardening filter, 70 kVp X-ray tube potential and maximum electron beam current of 210 mA, this time can be 25 μs and for a 20 μM layer of Er the time can almost double. At the target thickness of 150 μm, the time can increase to 520 μs. Long times to equilibrate can lead eventually to overheating of x-ray target 50.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method for producing an x-ray image of a human patient comprising:
    producing a beam of x-ray radiation from an x-ray source;
    selecting a region of interest in said human patient;
    controlling said beam to reduce said x-ray radiation emitted from areas of said x-ray source corresponding to areas outside said region of interest in said patient; and
    measuring amount of said x-ray radiation passing through said human patient and striking a detector.

2. The method of claim 1 further comprising:
    selecting a second region of interest in said human patient.

3. The method of claim 2 further comprising:
    reducing said x-ray radiation to areas outside said region of interest and said second region of interest.

4. The method of claim 2 further comprising:
    reducing said x-ray radiation to said second region of interest in said human patient.

5. The method of claim 1 further comprising:
    limiting said x-ray radiation to said region of interest in said human patient to a minimum amount required to achieve a specified signal-to-noise ratio.

6. The method of claim 1 further comprising:
    limiting said x-ray radiation to said region of interest in said human patient to a minimum amount required to achieve a specified resolution.

7. The method of claim 1 further comprising:
    limiting said x-ray radiation to areas outside said region of interest in said human patient to a minimum amount required to achieve a specified signal-to-noise ratio.

8. The method of claim 1 further comprising:
    limiting said x-ray radiation to areas outside said region of interest in said human patient to a minimum amount required to achieve a specified resolution.

9. The method of claim 1 further comprising:
    limiting said x-ray radiation to said region of interest in said human patient to a specified amount and less.

10. The method of claim 1 further comprising:
    terminating delivery of said x-ray radiation to said region of interest in said patient when said x-ray radiation to said region of interest reaches a predetermined threshold amount.

11. The method of claim 1 further comprising:
    selecting exposure of said x-ray radiation for each of a plurality of projections of said region of interest.

12. The method of claim 1 further comprising:
    reducing said x-ray radiation to areas outside said region of interest in said patient by decreasing an individual exposure time of said beam.

13. The method of claim 1 further comprising:
    reducing said x-ray radiation to areas outside said region of interest in said patient by decreasing a total number of exposures of said beam.

14. The method of claim 1 further comprising:
    adjusting said beam based on attenuation characteristics.

15. The method of claim 1 further comprising:
    compressing dynamic range by reducing said x-ray radiation to a translucent area in said human patient.

* * * * *